(12) United States Patent
Sliwa et al.

(10) Patent No.: US 11,179,194 B2
(45) Date of Patent: Nov. 23, 2021

(54) MEDICAL DEVICE WITH CONTACT FORCE SENSING TIP

(71) Applicant: St. Jude Medical, Cardiology Division, Inc., St. Paul, MN (US)

(72) Inventors: John W. Sliwa, San Jose, CA (US); Alon Izmirli, Ganot Hadar (IL)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 769 days.

(21) Appl. No.: 15/030,065

(22) PCT Filed: Dec. 10, 2014

(86) PCT No.: PCT/US2014/069521
§ 371 (c)(1),
(2) Date: Apr. 17, 2016

(87) PCT Pub. No.: WO2015/089173
PCT Pub. Date: Jun. 18, 2015

(65) Prior Publication Data
US 2016/0278852 A1    Sep. 29, 2016

Related U.S. Application Data

(60) Provisional application No. 61/915,212, filed on Dec. 12, 2013.

(51) Int. Cl.
*A61B 18/00*     (2006.01)
*A61B 5/06*      (2006.01)
(Continued)

(52) U.S. Cl.
CPC ............ *A61B 18/1492* (2013.01); *A61B 5/06* (2013.01); *A61B 5/062* (2013.01);
(Continued)

(58) Field of Classification Search
CPC .......... A61B 18/1492; A61B 2090/065; A61B 2018/00827; A61B 2018/00577;
(Continued)

(56) References Cited

U.S. PATENT DOCUMENTS

| | | | | |
|---|---|---|---|---|
| 5,425,367 | A | * | 6/1995 | Shapiro ................... A61B 5/06 |
| | | | | 128/899 |
| 5,725,367 | A | * | 3/1998 | Joshi ....................... F23D 14/22 |
| | | | | 239/424 |

(Continued)

FOREIGN PATENT DOCUMENTS

| | | |
|---|---|---|
| WO | 2012098551 | 7/2012 |
| WO | 2013/019544 | 2/2013 |

OTHER PUBLICATIONS

International Search Report for PCT Application No. PCT/US2014/069521, dated Mar. 9, 2015, 5 pgs.

*Primary Examiner* — Jaymi E Della
*Assistant Examiner* — Rachel A. Vierra
(74) *Attorney, Agent, or Firm* — Dykema Gossett PLLC

(57) ABSTRACT

A medical device for diagnosis or treatment of tissue in a body is provided. The device includes an elongate, tubular shaft configured to be received within the body. The shaft has a proximal portion and a distal portion configured for movement relative to the proximal portion. A flexible member having a predetermined stiffness is disposed between the proximal and distal portions. A plurality of coils are disposed within the shaft with one or more of the coils configured for movement with the distal portion. Electromagnetic fields generated from within or outside of the medical device induce currents in the coils from which movement of the distal portion in response to contact of the distal portion with the tissue may be determined. In one embodiment, several of the coils are connected in series to reduce the space required in the device for conductors.

9 Claims, 15 Drawing Sheets

(51) Int. Cl.
*A61B 18/14* (2006.01)
*A61B 90/00* (2016.01)

(52) U.S. Cl.
CPC ........... *A61B 2018/00577* (2013.01); *A61B 2018/00839* (2013.01); *A61B 2090/064* (2016.02); *A61B 2090/065* (2016.02); *A61B 2218/002* (2013.01); *A61B 2562/0247* (2013.01)

(58) Field of Classification Search
CPC .... A61B 2018/00839; A61B 2218/007; A61B 2218/002; A61B 2562/0247; A61B 5/683; A61B 5/3846; A61B 5/150954; A61B 2090/064; A61B 5/06; A61B 5/062; A61B 5/065
See application file for complete search history.

(56) References Cited

U.S. PATENT DOCUMENTS

| | | | | |
|---|---|---|---|---|
| 6,253,770 | B1* | 7/2001 | Acker | A61B 5/06 |
| | | | | 128/899 |
| 6,593,884 | B1* | 7/2003 | Gilboa | A61B 5/06 |
| | | | | 342/448 |
| 2001/0047133 | A1 | 11/2001 | Gilboa et al. | |
| 2002/0071358 | A1 | 6/2002 | Kim et al. | |
| 2008/0015551 | A1 | 1/2008 | Feine | |
| 2009/0018434 | A1* | 1/2009 | Kimura | A61B 5/062 |
| | | | | 600/424 |
| 2009/0138007 | A1 | 5/2009 | Govari et al. | |
| 2013/0303886 | A1* | 11/2013 | Ludwin | A61B 1/0008 |
| | | | | 600/424 |
| 2014/0187917 | A1* | 7/2014 | Clark | A61B 5/6852 |
| | | | | 600/424 |

\* cited by examiner

MEDICAL DEVICE WITH CONTACT FORCE SENSING TIP

CROSS-REFERENCE TO RELATED APPLICATIONS

This application claims the benefit of U.S. provisional application No. 61/915,212, filed 12 Dec. 2013, which is hereby incorporated by reference as though fully set forth herein.

BACKGROUND a. Field

This disclosure relates to a medical device and system for diagnosis or treatment of tissue in a body. In particular, the instant disclosure relates to a device and system that provides an indication of contact force between the device and the tissue.

b. Background Art

A wide variety of medical devices are inserted into the body to diagnose and treat various medical conditions. Catheters, for example, are used to perform a variety of tasks within human bodies and other bodies including the delivery of medicine and fluids, the removal of bodily fluids and the transport of surgical tools and instruments. In the diagnosis and treatment of atrial fibrillation, for example, catheters may be used to deliver electrodes to the heart for electrophysiological mapping of the surface of the heart and to deliver ablative energy to the surface among other tasks.

Some conventional catheters include components for determining the degree of contact between the catheter and tissue and for controlling the catheter in response to the degree of contact. In the case of an electrophysiological diagnostic mapping catheter, for example, sufficient contact is desirable to provide meaningful sensor outputs and accurate mapping of the heart. In the case of ablation catheters, sufficient contact is required for effective formation of ablative lesions in the tissue. A variety of mechanisms have been employed in catheters to determine contact force between catheters and tissue. Many of these mechanisms, however, are relatively complex and require additional components that increase the cost, size, and complexity of the catheter.

The foregoing discussion is intended only to illustrate the present field and should not be taken as a disavowal of claim scope.

SUMMARY

Among other things, various embodiments disclosed herein are directed to a medical device and a system for diagnosis or treatment of tissue in a body. In particular, the instant disclosure relates to a device and system that provide an indication of contact force between the device and the tissue.

A medical device for the diagnosis or treatment of tissue in a body in accordance with one embodiment of the present teachings includes an elongate, tubular shaft configured to be received within the body. The shaft has a proximal portion and a distal portion configured for movement relative to the proximal portion including by movement towards and away from the proximal portion along a longitudinal axis of the shaft and by deflection from the longitudinal axis. The device further includes a flexible member disposed between the proximal and distal portions of the shaft. The flexible member has a predetermined stiffness. The device further includes a first electromagnetic coil disposed within the shaft and a second electromagnetic coil disposed within the shaft and configured for movement with the distal portion of the shaft and relative to the first electromagnetic coil. The second electromagnetic coil is connected in series with the first electromagnetic coil at a common node. A device in accordance with this embodiment of the present teachings is advantageous relative to conventional devices because it provides a means for measuring contact force between the device and tissue in the body that is less complex and less expensive than conventional devices and systems. In particular, the use of series connected coils enables a contact force to be determined while reducing the number of conductors needed within the device as compared to conventional devices. As a result, the device conserves valuable space within the device. Further, the disclosed device is less expensive to manufacture.

A system for the treatment or diagnosis of tissue within a body in accordance with one embodiment of the present teachings includes a medical device, comprising an elongate, tubular shaft configured to be received within the body. The shaft has a proximal portion and a distal portion configured for movement relative to the proximal portion including by movement towards and away from the proximal portion along a longitudinal axis of the shaft and by deflection from the longitudinal axis. The device further includes a flexible member disposed between the proximal and distal portions of the shaft. The flexible member has a predetermined stiffness. The device further includes a first electromagnetic coil disposed within the shaft and a second electromagnetic coil disposed within the shaft and configured for movement with the distal portion of the shaft and relative to the first electromagnetic coil. The second electromagnetic coil is connected in series with the first electromagnetic coil at a common node. They system further includes an electronic control unit configured to determine a specific contact force between the distal portion of the shaft and the tissue responsive to signals generated by one or more of the first and second electromagnetic coils. A system in accordance with this embodiment of the present teachings is again advantageous relative to conventional systems because it provides a means for measuring contact force between the device and tissue in the body that is less complex and less expensive than conventional devices and systems. In particular, the use of series connected coils enables a contact force to be determined while reducing the number of conductors needed within the device as compared to conventional devices. As a result, the device conserves valuable space within the device. Further, the disposable device is less expensive to manufacture.

A medical device for the diagnosis or treatment of tissue in a body in accordance with another embodiment of the present teachings includes an elongate, tubular shaft configured to be received within the body. The shaft has a proximal portion and a distal portion configured for movement relative to the proximal portion including by movement towards and away from the proximal portion along a longitudinal axis of the shaft and by deflection from the longitudinal axis. The device further includes a flexible member disposed between the proximal and distal portions of the shaft. The flexible member has a predetermined stiffness. The device further includes first, second and third electromagnetic coils disposed within the shaft. Each of the first, second and third electromagnet coils has a first end and a second end. The first ends of the first, second and third electromagnetic coils are coupled to corresponding first, second and third conductors and the second ends of the first, second and third electromagnetic coils are coupled to a fourth conductor at a common node. The device further includes a fourth electromagnetic coil disposed within the shaft. The fourth electromagnetic coil has a first end coupled to a fifth conductor and a second end coupled to a sixth conductor. Either the first, second, and third electromagnetic coils or the fourth electromagnetic coil are configured for movement with the distal portion of the shaft and relative to the other of the first, second and third electromagnetic coils or the fourth electromagnetic coil. A device in accordance with this embodiment of the present teachings is advantageous relative to conventional devices because it provides a means for measuring contact force between the device and tissue in the body that is less complex and less expensive than conventional devices and systems. In particular, by coupling multiple coils at a common node and using a common conductor, the device enables a contact force to be determined while reducing the number of conductors needed within the device as compared to conventional devices. As a result, the device conserves valuable space within the device. Further, the disposable device is less expensive to manufacture.

A system for the diagnosis or treatment of tissue in a body in accordance with another embodiment of the present teachings includes a medical device having an elongate, tubular shaft configured to be received within the body. The shaft has a proximal portion and a distal portion configured for movement relative to the proximal portion including by movement towards and away from the proximal portion along a longitudinal axis of the shaft and by deflection from the longitudinal axis. The device further includes a flexible member disposed between the proximal and distal portions of the shaft. The flexible member has a predetermined stiffness. The device further includes first, second and third electromagnetic coils disposed within the shaft. Each of the first, second and third electromagnet coils has a first end and a second end. The first ends of the first, second and third electromagnetic coils are coupled to corresponding first, second and third conductors and the second ends of the first, second and third electromagnetic coils are coupled to a fourth conductor at a common node. The device further includes a fourth electromagnetic coil disposed within the shaft. The fourth electromagnetic coil has a first end coupled to a fifth conductor and a second end coupled to a sixth conductor. Either the first, second, and third electromagnetic coils or the fourth electromagnetic coil are configured for movement with the distal portion of the shaft and relative to the other of the first, second and third electromagnetic coils or the fourth electromagnetic coil. The system further includes an electronic control unit configured to determine a specific contact force between the distal portion of the shaft and the tissue responsive to signals generated by one or more of the first, second, third and fourth electromagnetic coils. A system in accordance with this embodiment of the present teachings is advantageous relative to conventional systems because it provides a means for measuring contact force between the device and tissue in the body that is less complex and less expensive than conventional devices and systems. In particular, by coupling multiple coils at a common node and using a common conductor, the device enables a contact force to be determined while reducing the number of conductors needed within the device as compared to conventional devices. As a result, the device conserves valuable space within the device. Further, the disposable device is less expensive to manufacture.

A system for the treatment or diagnosis of tissue within a body in accordance with another embodiment of the present teachings includes a medical device comprising an elongate, tubular shaft configured to be received within the body. The shaft has a proximal portion and a distal portion configured for movement relative to the proximal portion including by movement towards and away from the proximal portion along a longitudinal axis of the shaft and by deflection from the longitudinal axis. The device further includes a flexible member disposed between the proximal and distal portions of the shaft. The flexible member has a predetermined stiffness. The device further includes first, second, third and fourth electromagnetic coils disposed within the shaft. Either the first electromagnetic coil or the second, third and fourth electromagnetic coils are configured for movement with the distal portion of the shaft and relative to the other of the first electromagnetic coil or the second, third and fourth electromagnetic coils. The system further includes an electronic control unit. The electronic control unit is configured to generate a first current in the first electromagnetic coil to create a first electromagnetic field and to generate a second current in the second electromagnetic coil to create a second electromagnetic field opposing the first electromagnetic field. The electronic control unit is further configured to measure an electrical characteristic associated with the second electromagnetic coil, the electrical characteristics indicative of deformation of the flexible member and a specific contact force between the distal portion and the tissue. A system in accordance with this embodiment of the present teachings is more sensitive relative to conventional systems because it eliminates the effect of magnetic coupling between the coils that exists in the absence of any contact force and deflection.

A system for the treatment or diagnosis of tissue within a body in accordance with another embodiment of the present teachings includes a medical device comprising an elongate, tubular shaft configured to be received within the body. The shaft has a proximal portion and a distal portion configured for movement relative to the proximal portion including by movement towards and away from the proximal portion along a longitudinal axis of the shaft and by deflection from the longitudinal axis. The device further includes a flexible member disposed between the proximal and distal portions of the shaft. The flexible member has a predetermined stiffness. The device further includes first, second, third and fourth electromagnetic coils disposed within the shaft. Either the first electromagnetic coil or the second, third and fourth electromagnetic coils are configured for movement with the distal portion of the shaft and relative to the other of the first electromagnetic coil or the second, third and fourth electromagnetic coils. The system further includes an electronic control unit configured to generate a current in the first electromagnetic coil, to determine a change in an electrical characteristic associated with the second electromagnetic coil over a period of time of decay in an electromagnetic field and to integrate the change in the electrical characteristic to obtain an integrated value of a coupled field strength of the electromagnetic field. The integrated value is indicative of an amount of deformation of the flexible member.

A system for the treatment or diagnosis of tissue within a body in accordance with another embodiment of the present teachings includes a medical device, comprising an elongate, tubular shaft configured to be received within the body. The shaft has a proximal portion and a distal portion configured for movement relative to the proximal portion including by movement towards and away from the proximal portion along a longitudinal axis of the shaft and by deflection from the longitudinal axis. The device further includes a flexible member disposed between the proximal and distal portions of the shaft. The flexible member has a predetermined stiffness. The device further includes first, second, third and fourth electromagnetic coils disposed within the shaft. Either the first electromagnetic coil or the second, third and fourth electromagnetic coils are configured for movement with the distal portion of the shaft and relative to the other of the first electromagnetic coil or the second, third and fourth electromagnetic coils. The system further includes a magnetic field generator disposed outside of the medical device and configured to generate a first electromagnetic field. The system further includes an electronic control unit configured to determine a first position for each of the first, second, third and fourth electromagnetic coils responsive to currents induced in the first, second, third and fourth electromagnetic coils by the first electromagnetic field. The electronic control unit is further configured to generate a current in the first electromagnetic coil to create a second electromagnetic field and to determine a second position of the first electromagnetic coil responsive to currents induced in the second, third and fourth electromagnetic coils by the second electromagnetic field. The electronic control unit is further configured to determine a contact force between the distal portion of the shaft and the tissue responsive to the first positions of the first, second, third and fourth electromagnetic coils and the second position of the first electromagnetic coil. A system in accordance with this embodiment of the present teachings is advantageous as compared to conventional systems because the system improves the accuracy of contact force measurements by using position information from multiple field generators both within and outside of the medical device.

The foregoing and other aspects, features, details, utilities, and advantages of the present teachings will be apparent from reading the following description and claims, and from reviewing the accompanying drawings.

DETAILED DESCRIPTION OF EMBODIMENTS

Various embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a physician manipulating one end of an instrument used to treat a patient. The term "proximal" refers to the portion of the instrument closest to the physician and the term "distal" refers to the portion located furthest from the physician. Similarly, "more proximal" means closer to the physician whereas "more distal" means further form the physician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
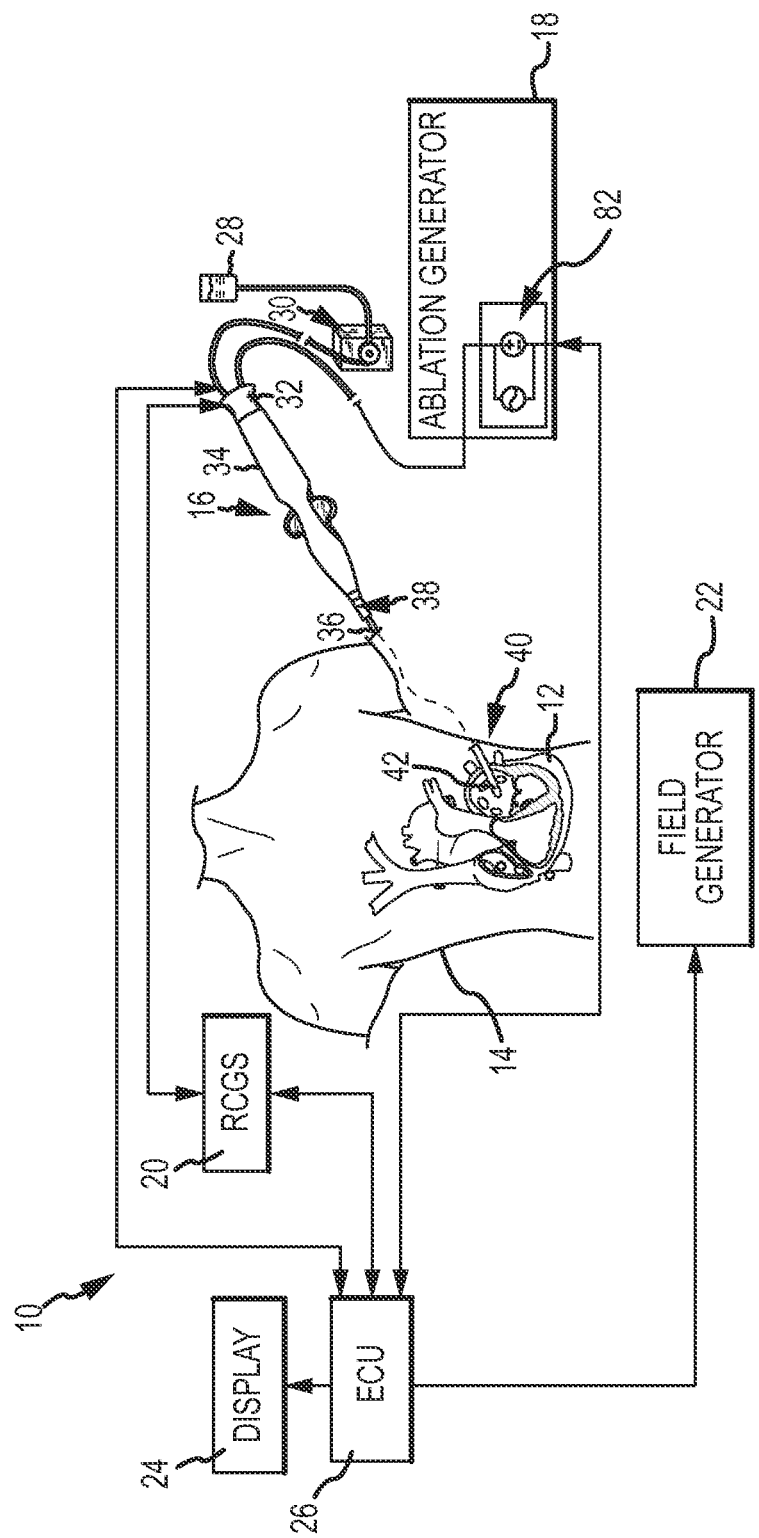
FIG. 1 is diagrammatic view of a system for diagnosis or treatment of tissue in a body in accordance with one embodiment of the present teachings.

Referring now to the drawings wherein like reference numerals are used to identify identical or similar components in the various views, FIG. 1 illustrates one embodiment of a system 10 for diagnosis or treatment of tissue 12 in a body 14. In the illustrated embodiment, tissue 12 comprises cardiac tissue within a human body. It should be understood, however, that a system 10 in accordance with the present teachings may find application in connection with procedures for the diagnosis or treatment of a variety of tissues in human and non-human bodies. System 10 includes a medical device for diagnosis or treatment of tissue 12. In accordance with one embodiment, system 10 includes an ablation catheter 16 for diagnosis or treatment of tissue 12 and may further include an ablation generator 18, a remote catheter guidance system (RCGS) 20, an external field generator 22, a display system 24, and/or an electronic control unit (ECU) 26.

Figure 2:
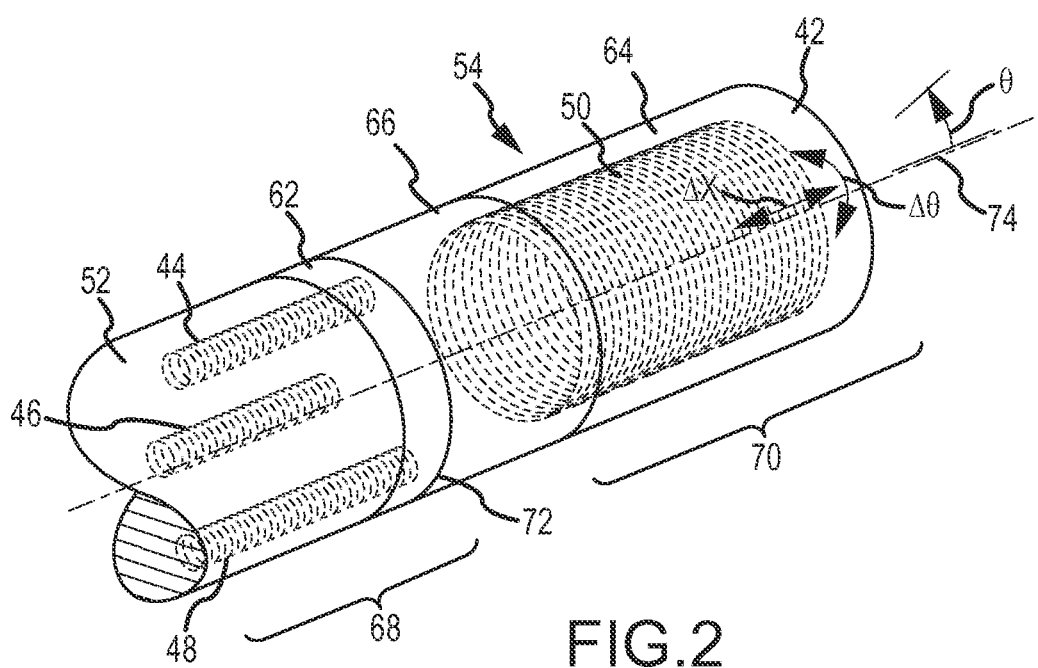
FIG. 2 is a isometric view of a portion of a medical device for diagnosis or treatment of tissue in accordance with one embodiment of the present teachings.
Figure 3:
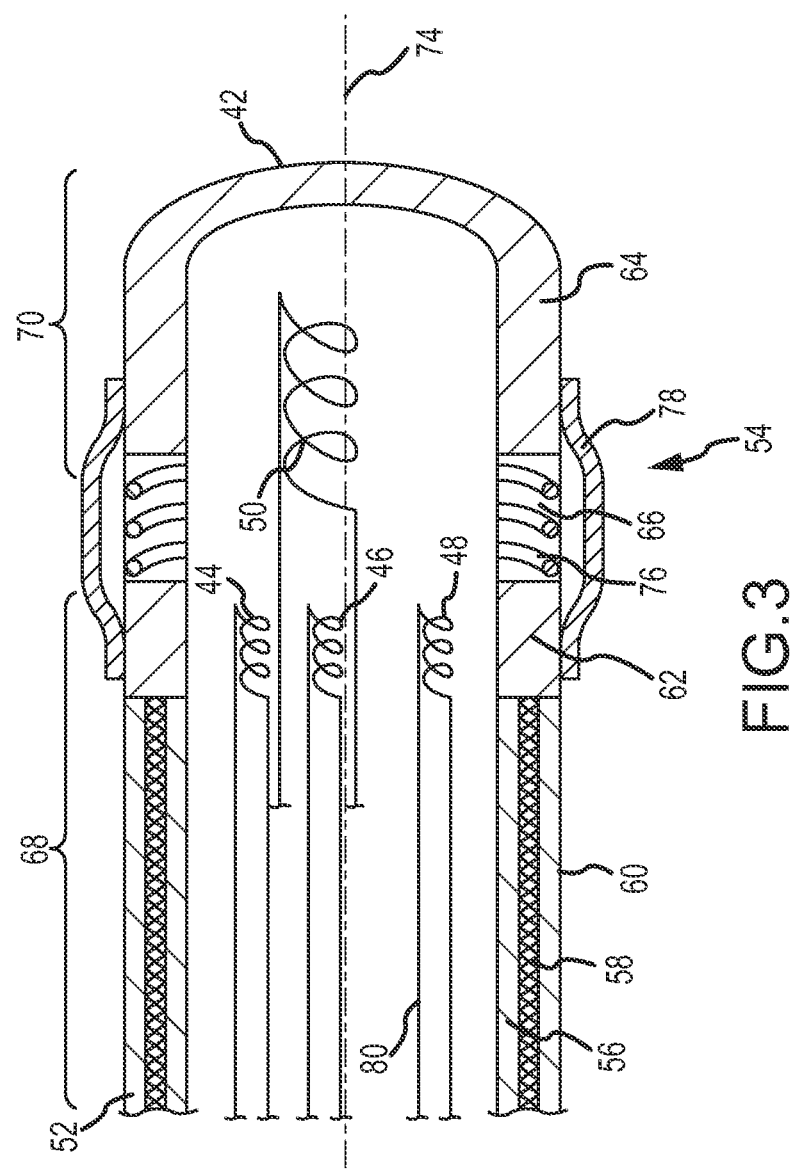
FIG. 3 is a sectional view illustrating portions of the medical device of FIG. 2.

Catheter 16 is provided for examination, diagnosis and treatment of internal body tissues such as tissue 12. In accordance with one embodiment of the present teachings, catheter 16 comprises an ablation catheter and, more particularly, an irrigated radio-frequency (RF) ablation catheter. It should be understood, however, that catheter 16 is provided for illustration only and that system 10 could be adapted for use with other types of catheters including electrophysiology (EP) mapping catheters and intracardiac echocardiograph (ICE) catheters, as well as for use with other types of ablation catheters including those providing different types of ablation energy (e.g., cryoablation, ultrasound, laser, microwave, electroporation, etc.) and/or those sized and configured to access different areas of a patient's body or cardiovascular system, such as, for example, renal arteries. Further, it should be understood that system 10 can be adapted for use with other types of medical devices used in the diagnosis or treatment of tissue 12 including, for example, introducer sheaths. Catheter 16 may be connected to an irrigant fluid source 28 having a biocompatible fluid such as saline which is passed through an irrigation pump 30 (which may comprise, for example, a fixed rate roller pump or variable volume syringe pump with a gravity feed supply from fluid source 28 as shown) for irrigation. Catheter 16 may also be electrically connected to ablation generator 18 for delivery of ablating RF energy. Catheter 16 may include a cable connector or interface 32, a handle 34, a flexible shaft 36 having a proximal end 38 and a distal end 40 and one or more ablation and sensing electrodes 42. Catheter 16 may also include other conventional components not illustrated herein such as a temperature sensor, additional pacing or mapping electrodes, and corresponding conductors or leads. Referring to FIGS. 2-3, in accordance with the present teachings, catheter 16 may further include means, such as electromagnetic coils 44, 46, 48, 50 for sensing a contact force of the distal end 40 of catheter 16 with tissue 12.

Referring again to FIG. 1, connector 32 provides mechanical, fluid and electrical connection(s) for cables extending from ablation generator 18, RCGS 20, and pump 30. Connector 32 is conventional in the art and is disposed at a proximal end of catheter 16. Although directly attached to handle 34 in the illustrated embodiment, connector 32 may be coupled to handle 34 indirectly through, for example, several feet of cable.

Handle 34 provides a location for the physician to hold catheter 16 and may further provides means for steering or guiding shaft 36 within body 14. For example, handle 34 may include means to change the length of a steering wire extending through catheter 16 to distal end 40 of shaft 36 to control translation and/or deflection of the distal end 40 of shaft 36 to bendably steer shaft 36. Handle 34 may be manipulated manually by a physician or automatically through, for example, robotic controls such as RCGS 20. It should be understood that the construction of handle 34 may vary and may be absent in a fully-robotic implementation of the system.

Shaft or flexible lumen 36 provides structural support to other components of catheter 16 including electrodes 42, coils 44, 46, 48, 50, wires and other conductors extending to electrodes 42 and coils 44, 46, 48, 50 and possibly additional electronics used for signal processing or conditioning. Shaft 36 may also permit transport, delivery, and/or removal of fluids (including irrigation fluids and bodily fluids), medicines, and/or surgical tools or instruments. Shaft 36 is configured to be received within body 14 and may be introduced into a blood vessel or other structure within body 14 through a conventional introducer. Shaft 36 may then be steered or guided through body 14 to a desired location such as tissue 12 with a guiding introducer such as the Agilis™ NxT steerable introducer available from St. Jude Medical, Inc., with RCGS 20, or with guide wires, pullwires or other means known in the art. Referring to FIGS. 2-3, shaft 36 may include an elongate, tubular member 52 and a tip assembly 54.

Member 52 is flexible or deformable and configured for movement within body 14 (FIG. 1). Member 52 also defines one or more lumens configured to house conductors and steering wires and to allow fluids to pass therethrough. Referring to FIG. 3, member 52 may include a tubular, polymeric inner liner 56, a braided wire layer 58 for torque transfer, and an outer polymeric jacket 60. Liner 56 may be made from a polymeric material such as polyfluoroethylene (PTFE) including PTFE sold under the registered trademark "TEFLON" by E. I. DuPont de Nemours & Co. Corp, polyether block amides, nylon or thermoplastic elastomers such as the elastomer sold under the registered trademark "PEBAX" by Arkema, Inc. Braided wire layer 58 is configured to provide appropriate levels of pushability, torqueability, flexibility, and kink resistance to shaft 36. Layer 58 may be formed from stainless steel wire, and may be flat wire (wire having a cross-section that, when taken along the wire's longitudinal axis and measured along two orthogonal axes, is substantially rectangular) arranged in various braid patterns including one-over-one (involving at least two wires) or two-over-two (involving at least four wires) crossover patterns. The wire may be coated with a layer of an insulating material. The wire braid may be directly wound about liner 56 or placed on a core that is slid over liner 56. Jacket 60 is made from a polymeric material such as polyfluoroethylene (PTFE) including PTFE sold under the registered trademark "TEFLON" by E. I. DuPont de Nemours & Co. Corp, polyether block amides, nylon or thermoplastic elastomers such as the elastomer sold under the registered trademark "PEBAX" by Arkema, Inc. and may be extruded over layer 58. Additional details regarding several exemplary catheter constructions may be found in commonly assigned U.S. Pat. No. 7,914,515, the entire disclosure of which is incorporated herein by reference. Member 52 may further be configured to receive tip assembly 54 at a distal end of member 52.

Figure 4:
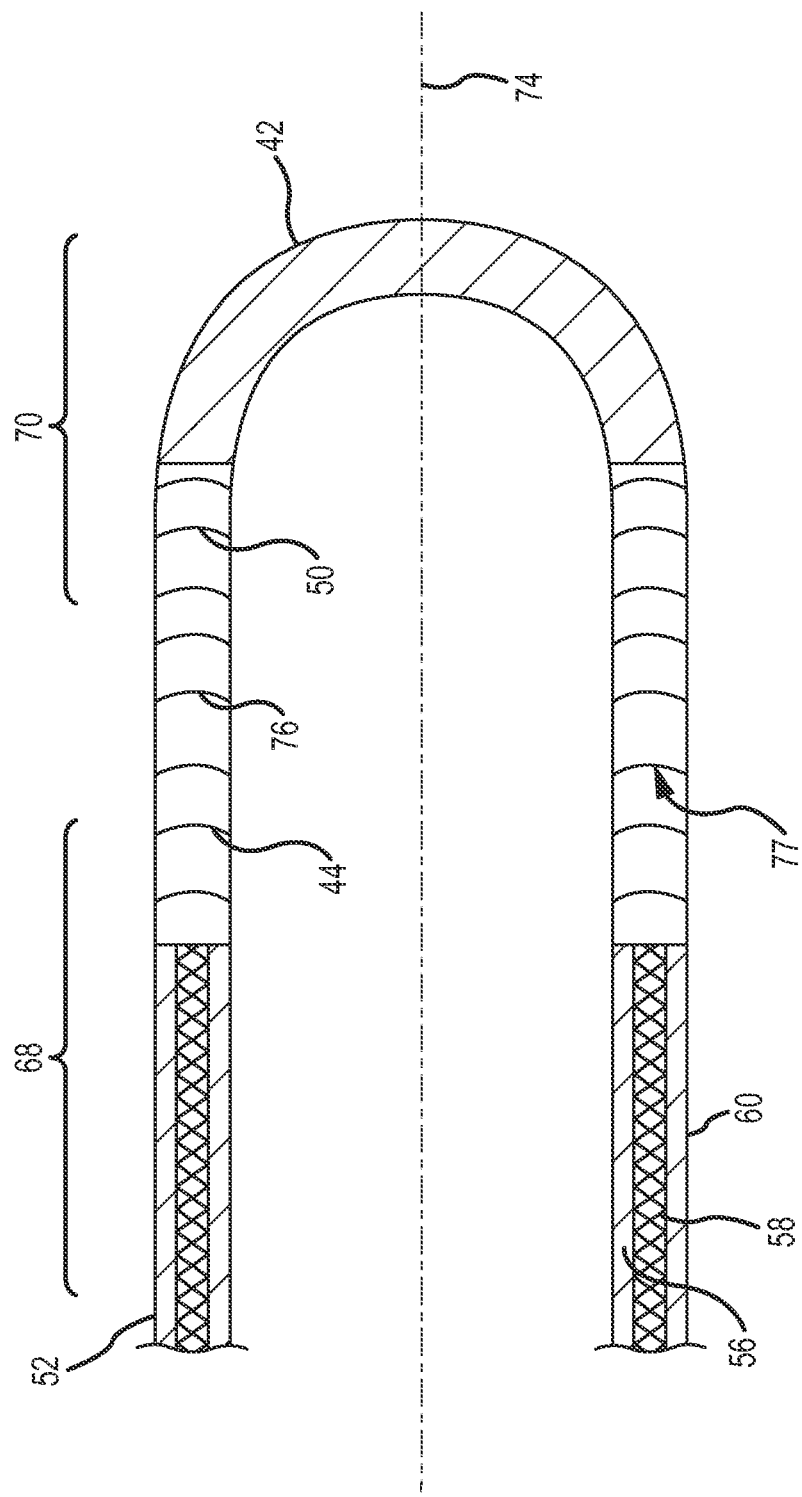
FIG. 4 is a sectional view illustrating portions of a medical device in accordance with another embodiment of the present teachings.

Tip assembly 54 includes a more proximal tip portion 62, a more distal tip portion 64 and an intermediate tip portion 66 between portions 62, 64. Proximal tip portion 62 is configured for mounting tip assembly 54 to member 52 at a distal end of member 52. Proximal tip portion 62 extends from the distal end of member 52 to intermediate tip portion 66. Proximal tip portion 62 may be made from a material or materials that are relatively rigid and at least more rigid than materials used to form intermediate tip portion 66 which has a finite controlled flexibility such as found in a spring. Together with member 52, proximal tip portion 62 may form a proximal portion 68 of shaft 36. Distal tip portion 64 may comprise, or may be configured to support, electrode 42. Distal tip portion 64 extends from an opposite side of intermediate tip portion 66 relative to proximal tip portion 62. Distal tip portion 64 may also be made from a material or materials that are relatively rigid and at least more rigid than materials used to form flexible intermediate tip portion 66. Distal tip portion 64 forms a distal portion 70 of shaft 36. Intermediate tip portion 66 provides a means for allowing movement of the distal portion 70 of shaft 36 relative to a distal end 72 of proximal portion 68 of shaft 36 including movement towards and away from distal end 72 of proximal portion 68 along a longitudinal axis 74 of shaft 36 and by bending deflection from axis 74. Intermediate tip portion 66 is made from a material or materials that are relatively flexible and at least more flexible than materials used to form proximal and distal tip portions 62, 64. Intermediate tip portion 66 defines or includes a flexible member such as a spring 76 or elastomeric bending rods having at least one predetermined or known stiffness (i.e., a measure of deformation such as grams per degree or grams per millimeter during at least one specific deformation state such as bending, compression, etc.) such that deformation behavior of the flexible member in response to force is known and a detected deformation can be translated to a force by using a look-up table or other data structure in a memory or by using an algorithm. Spring 76 may comprise a helical, coiled, wave or bellows spring and may be made from a variety of materials including metals and metal alloys such as stainless steel, titanium, beryllium-copper, nickel titanium (Nitinol) and Invar as well as elastomeric polymers. Spring 76 may also be formed using subtractive laser etching or, electrical discharge machining as from a metal cylindrical tube. Intermediate tip portion 66 may include a single spring 76 centered about axis 74 or a plurality of springs disposed about axis 74 (e.g., three springs spaced equally circumferentially about axis 74). In place of spring 76, intermediate tip portion 66 may alternatively be formed from elastomeric materials including, for example, rubber, such that the flexible element is formed as a small deformable disc, torus or bendable rod. Referring to FIG. 4, in another alternative embodiment, the flexible member such as spring 76 in intermediate tip portion 66 may be formed as part of a unitary coil 77 along with, for example, coil 44 and with coil 50. Coils 44, 50 are disposed at opposite ends of unitary coil 77 with the portion of coil 77 forming coil 44 fixed in position. Spring 76 is disposed intermediate the opposite ends of coil 77. Thus, coils 44, 50 are at least electromagnetic coils but optionally may also contribute to calibrated spring behavior. Similarly, spring 76 is at least a calibrated spring but optionally may also contribute to electromagnetic coil behavior. Referring again to FIG. 3, tip assembly 54 may further include an easily flexible thin sleeve 78 surrounding intermediate tip portion 66 to prevent ingress of blood from body 14 into the interior of tip assembly 54 and/or egress of saline or other fluids from the interior of tip assembly 54 into the body 14. Sleeve 78 may be sealed to exterior surfaces of tip assembly 54 near the distal end of proximal tip portion 62 and the proximal end of distal tip portion 64. Sleeve 78 may be made, for example, from a highly flexible thin elastomeric material. Sleeve 78 may be formed and mounted so as not to alter the predetermined stiffness of spring 76 or similar flexible member (either in axial compression or bending) or at least minimize any impact on the predetermined stiffness of spring 76 or similar flexible member. Accordingly, sleeve 78 may be selected so that its shape, configuration and material properties have a minimal or no impact on the stiffness of spring 76 or similar flexible member and so that the any stiffness of sleeve 78 does not vary, or has relatively little variation, despite changes in temperature in tip member 54 and prolonged exposure to blood, saline or other fluids in body 14 and catheter 16. Accordingly, sleeve 78 may be configured so that any stiffness of sleeve 78 is less than 10% of the stiffness of spring 76 in one embodiment, and in another embodiment less than 5% of the stiffness of spring 76 and, in yet another embodiment, less than 2% of the stiffness of spring 76. Sleeve 78 may also be configured by material selection or application of coatings so that it has very low water absorption to prevent swelling of sleeve 78 and changes in size and stiffness. In particular, sleeve 78 may be configured so that its fluid absorption is less than 10% by weight and, in one embodiment, less than 5% by weight and, in another embodiment, less than 2% by weight. Sleeve 78 may also be formed with corrugations to reduce stiffness. Sleeve 78 may also be formed as a relatively thin walled deformable membrane (or balloon) that can be selectively urged away from spring 76 through fluid (e.g., saline) inflation.

Referring again to FIG. 1, electrodes 42 on the outer surface of member 52 or tip portion 54 are provided for a variety of diagnostic and therapeutic purposes including, for example, electrophysiological studies, catheter identification and location, pacing, and cardiac mapping and ablation. In the illustrated embodiment, catheter 16 includes an ablation tip electrode 42 at distal end 40 of shaft 36 that functions as an radio-frequency ablation delivery element. Catheter 16 may also include one or more ring electrodes (not shown) proximal of tip electrode 42 that may be used to obtain electrograms for tissue 12 and for other conventional purposes. It should be understood, however, that the number, orientation, and purpose of electrodes 42 may vary. Electrodes 42 may be made from various electrically conductive materials including those containing gold, platinum, iridium, palladium, rhodium, stainless steel, and/or any combination thereof.

Referring again to FIGS. 2-3, electromagnetic coils 44, 46, 48, 50 provide a means for sensing contact force between distal portion 70 of shaft 36 and tissue 12 (see FIG. 1) and therefore together form a force sensor. Current provided to one or more of coils 44, 46, 48, 50 creates magnetic fields that impact the inductance or other electrical characteristics of the other coils 44, 46, 48, 50. These characteristics are influenced by the position of coils 44, 46, 48 relative to coil 50. Therefore, measuring or detecting the magnetic fields of each coil 44, 46, 48, 50 such as by detecting the growth, steady state or decay of those fields, permits one to determine the position of coil 50 and distal tip portion 70 of shaft 36 relative to coils 44, 46, 48. These measurements may be made using various circuits for sensing current, voltage or resonant frequencies. In the embodiment illustrated in FIGS. 2-3, coils 44, 46, 48 are disposed in proximal portion 68 of shaft 36 while coil 50 is disposed in the distal portion 70 of shaft 36 and configured for movement with distal portion 70 of shaft 36 relative to the proximal portion 68 of shaft 36 and coils 44, 46, 48. It should be understood that the positions of coils 44, 46, 48 and coil 50 may be reversed such that one or more coils 44, 46, 48 could alternatively be disposed in distal portion 70 while coil 50 is disposed in proximal portion 68. Further, although coils 44, 46, 48 and coil 50 are shown in FIGS. 2-3 as disposed entirely within proximal tip portion 62 or distal tip portion 64, it should be understood that one or more of coils 44, 46, 48, 50 may at least partially extend into intermediate tip portion 66 to reduce the axial length of the force sensor. Coils 44, 46, 48, 50 may be disposed about stationary internal ferrite cores to increase the inductance of coils 44, 46, 48, 50. Coils 44, 46, 48, 50 may be coupled to ECU 26 using conventional conductors 80 (see FIG. 3) extending from proximal end 38 of shaft 36.

Figure 5:
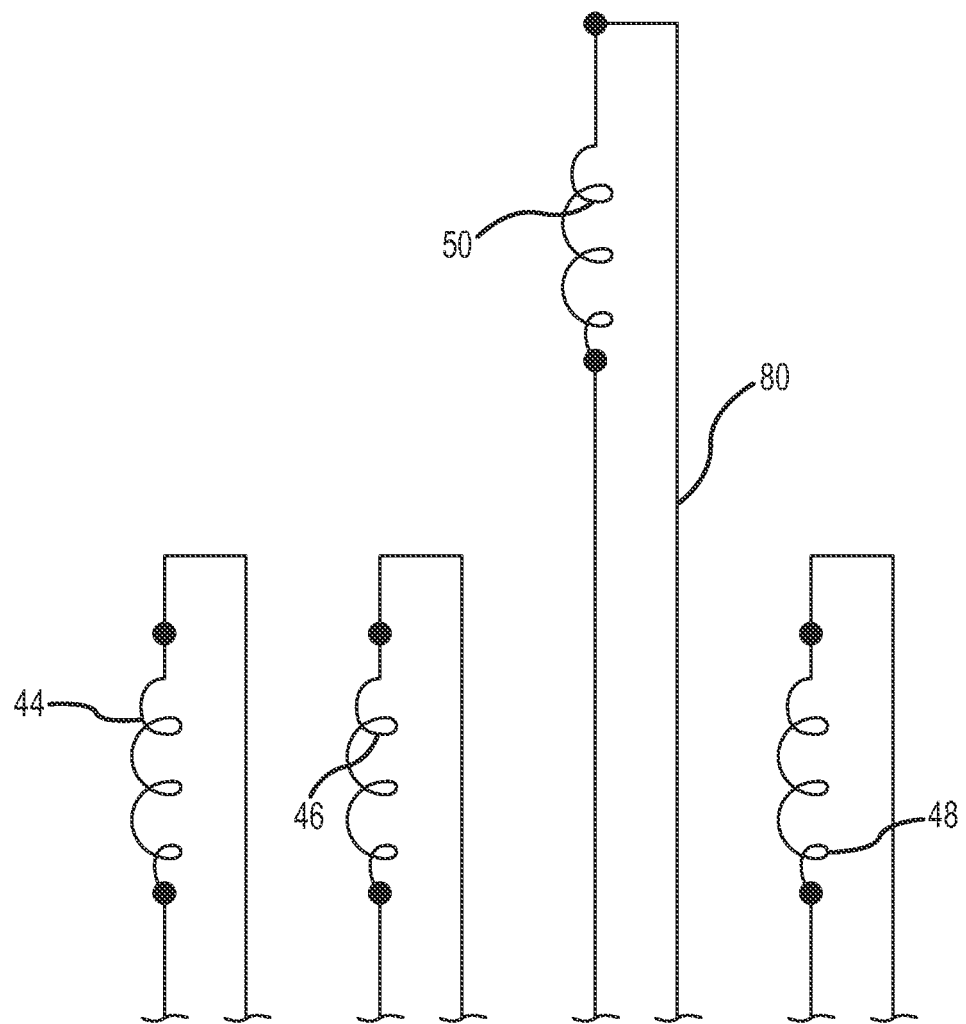
FIG. 5 is a circuit diagram illustrating a method of wiring the electromagnetic coils in the medical device of FIGS. 2-3 in accordance with certain embodiments of the present teachings.
Figure 6:
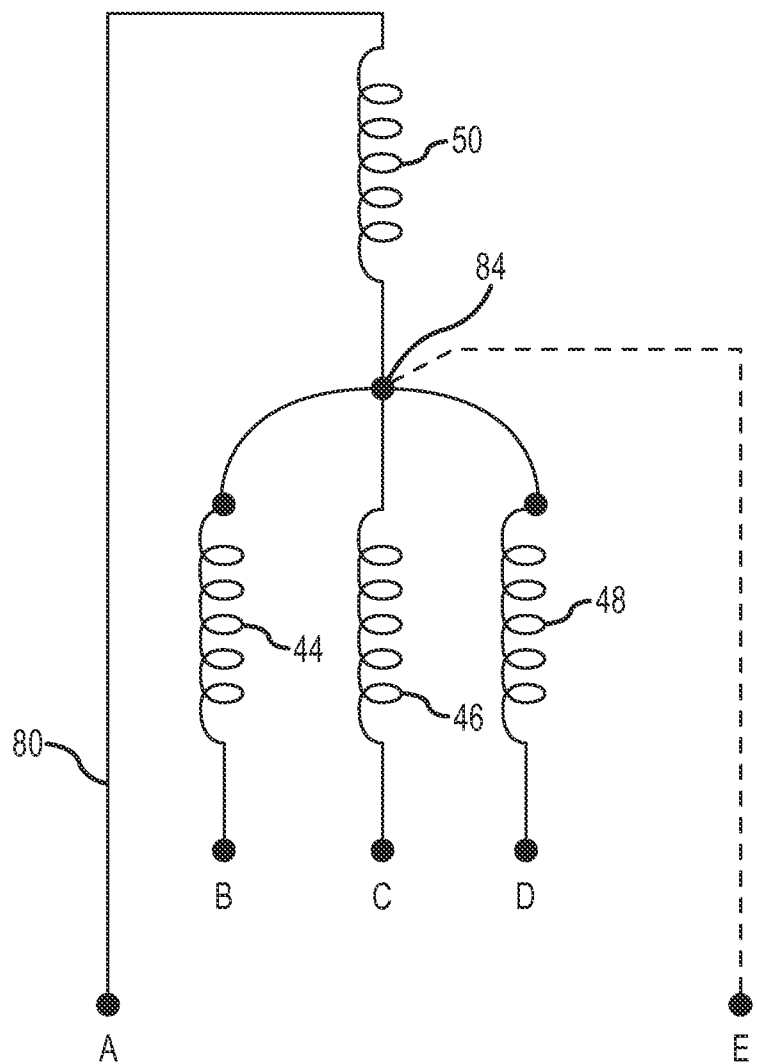
FIG. 6 is a circuit diagram illustrating another method of wiring the electromagnetic coils in the medical device of FIGS. 2-3 in accordance with other embodiments of the present teachings.
Figure 7:
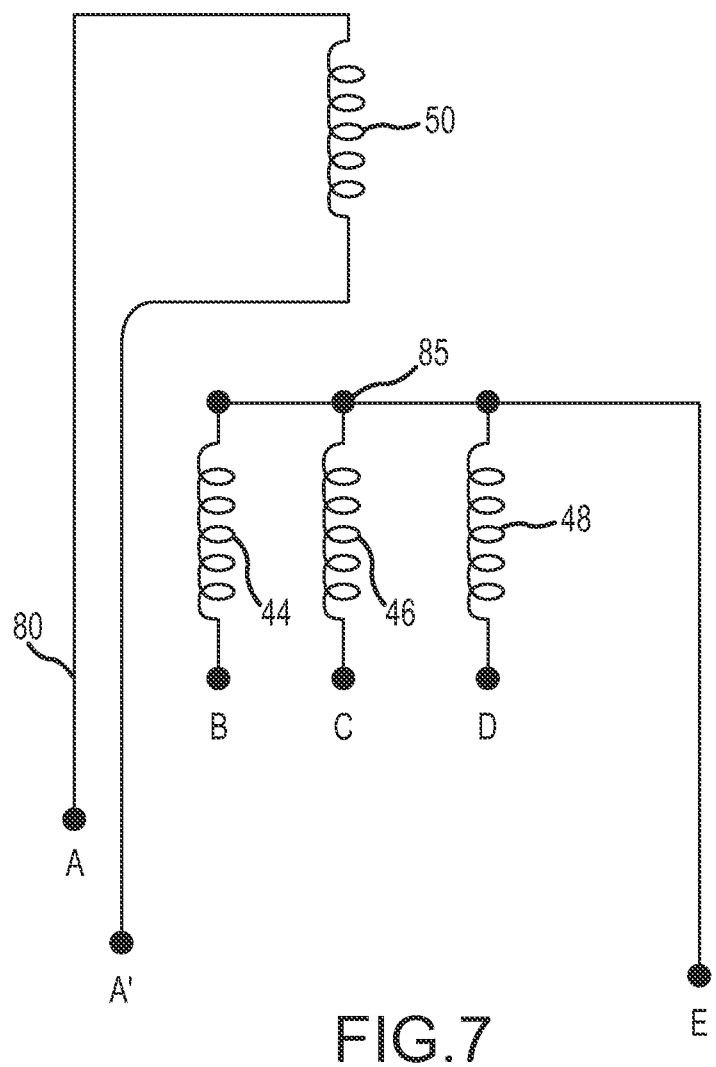
FIG. 7 is a circuit diagram illustrating another method of wiring the electromagnetic coils in the medical device of FIGS. 2-3 in accordance with other embodiments of the present teachings.

Referring to FIG. 5, in accordance with certain embodiments disclosed herein, separate conductors 80 may be coupled to each end of each coil 44, 46, 48, 50. Referring to FIG. 6, in accordance with certain alternative embodiments disclosed herein, coil 50 may be connected in series with each of coils 44, 46, 48. In particular, one end of coil 50 is connected with one end of each of coils 44, 46, 48 at a common node 84. The resulting force sensor provides a less complex and less expensive means for measuring contact force between catheter 16 and tissue 12. In particular, the use of series connected coils 44, 46, 48, 50 enables a contact force to be determined while reducing the number of conductors 80 needed within the device as compared to conventional devices. As a result, the device conserves valuable space within the device and is less expensive to manufacture. In the illustrated embodiment, four conductors 80 are used with one conductor 80 coupled to the end of each coil 44, 46, 48, 50 opposite the end of coil 44, 46, 48, 50 coupled to node 84. In certain embodiments, a fifth conductor 84 may also be coupled at node 84 for a purpose discussed hereinbelow. Referring to FIG. 7, in accordance with certain alternative embodiments disclosed herein, coils 44, 46, 48 may be coupled at a common node 85. The resulting force sensor again provides a less complex and less expensive means for measuring contact force between catheter 16 and tissue 12 by reducing the number of conductors 80 needed within the device as compared to conventional devices. In the illustrated embodiment, six conductors 80 are used including conductors coupled to each end of coil 50, conductors 80 coupled to one end of each of coils 44, 46, 48 and a conductor 80 coupled to node 85.

Figure 8:
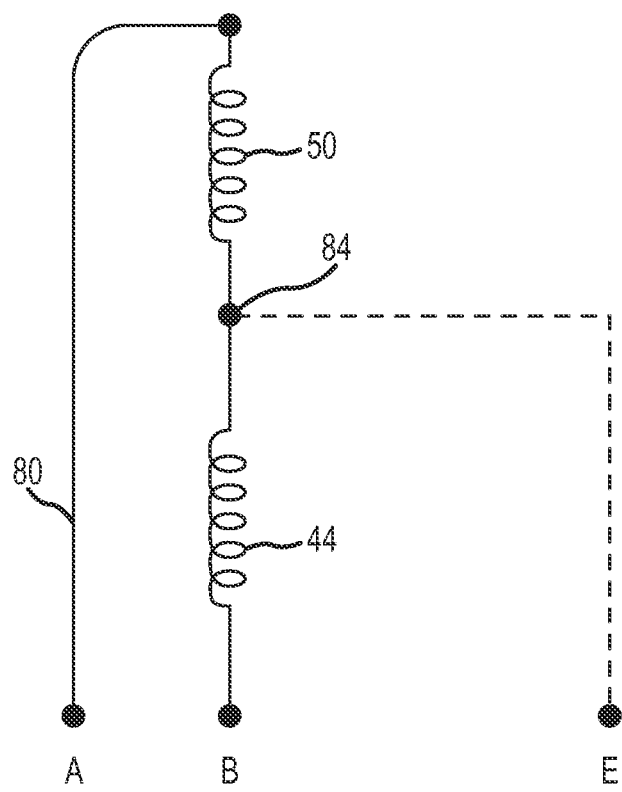
FIG. 8 is a circuit diagram illustrating another method of wiring the electromagnetic coils in the medical device of FIGS. 2-3 in accordance with other embodiments of the present teachings.

In the illustrated embodiment, coils 44, 46, 48 are disposed in proximal tip portion 62 of tip assembly 54 and may further at least partially extend into intermediate tip portion 66 to lessen the distance between coils 44, 46, 48 and coil 50. Coils 44, 46, 48 may alternatively be disposed in member 52 provided that coils 44, 46, 48 are prohibited from bending through, for example, placement in lumens formed in member using a rigid polymer. Coils 44, 46, 48 may be equally spaced circumferentially about axis 74 and may extend parallel to one another and axis 74. Coils 44, 46, 48 may be oriented in the same way. Alternatively, coils 44, 46, 48 may be oriented or wound in opposite directions for a purpose described hereinbelow. Although three coils 44, 46, 48 are shown in proximal portion 68 in the illustrated embodiment, it should be understood that the number of coils may vary depending on the degree of precision and the components of force to be determined In particular, a single coil 44, 46 or 48 may be employed and provide a measure of contact force. Referring to FIG. 8, for example, the embodiment shown in FIG. 6 may be replaced with a coil arrangement including only coils 44, 50 connected in series at node 84 thereby reducing the number of conductors 80 to as few as two or three conductors 80 in certain embodiments. The use of three coils 44, 46, 48, however, allows a determination of the deformation of the distal end 40 of catheter 16 in three-dimensional space and, therefore, the provision of a three-dimensional force vector representing the contact force.

Coils 44, 46, 48 generate signals indicative of the position of coils 44, 46, 48 relative to coil 50 and, therefore, indicative of the position of distal tip portion 70 of catheter 16. The axial and angular position of coil 50 relative to coils 44, 46, 48 effects various electrical characteristics of coils 44, 46, 48 when one or more of coils 44, 46, 48, 50 are excited. Movement of distal portion 70 of shaft 36 and, therefore, movement of coil 50 will result in a change in an electrical characteristic of each coil 44, 46, 48 that is indicative of a specific deformation of distal portion 70 of shaft 36 and also a specific contact force between the distal portion 70 of shaft 36 and tissue 12. For example, movement of coil 50 will cause a change in inductance in each coil 44, 46, 48. In particular, if intermediate tip portion 66 is compressed axially in response to contact of the distal end 40 of shaft 36 with tissue 12, the inductance in each coil 44, 46, 48 will increase as coil 50 moves closer to coils 44, 46, 48. If distal tip portion 64 bends relative to axis 74 in response to contact of the distal end 40 of shaft 36 with tissue 12, the inductance in certain coils 44, 46, 48, will increase while the inductance in other coils 44, 46, 48, will decrease as coil 50 moves closer to certain coils 44, 46, 48 and farther away from other coils 44, 46, 48 and angulates relative to the coils 44, 46 48.

Referring again to FIG. 1, ablation generator 18 generates, delivers and controls radiofrequency energy used by catheter 16. Generator 18 includes a radiofrequency generator 82 configured to generate an ablation signal that is output across a pair of source connectors: a positive polarity connector which may connect to electrode 42 on catheter 16; and a negative polarity connector which may be electrically connected by conductors or lead wires to a patch electrode (not shown) on body 14. It should be understood that the term connectors as used herein does not imply a particular type of physical interface mechanism, but is rather broadly contemplated to represent one or more electrical nodes. Generator 18 is configured to generate a signal at a predetermined frequency in accordance with one or more user specified parameters (e.g., power, time, etc.) and under the control of various feedback sensing and control circuitry as is know in the art. Ablation generator 18 may also monitor various parameters associated with the ablation procedure including impedance, the temperature at the tip of catheter 16, ablation energy and the position of the catheter 16 and provide feedback to the physician regarding these parameters.

RCGS 20 may be provided to manipulate catheter 16. In particular, RCGS 20 permits control of translation, distal bending, and virtual rotation of catheter 16 and any surrounding sheath. RCGS 20 therefore provides the user with a type of control similar to that provided by conventional manually-operated systems, but allows for repeatable, precise, and dynamic movements. A physician may identify target locations (potentially forming a path) on an image of tissue 12. RCGS 20 relates these digitally selected points to positions within the patient's actual/physical anatomy, and may thereafter command control the movement of catheter 16 to the defined positions where the physician or the RCGS 20 can perform the desired diagnostic of therapeutic function. A more complete description of various elements of an RCGS may be found in the following patent applications that are incorporated herein by reference in their respective entireties: International Patent Application Publication No. WO 2009/120982 published Oct. 1, 2009; U.S. Patent Application Publication No. 2009/0247942 published Oct. 1, 2009; U.S. Patent Application Publication No. 2009/0247944 published Oct. 1, 2009; U.S. Patent Application Publication No. 2009/0247993 published Oct. 1, 2009; U.S. Patent Application Publication No. 2009/0248042 published Oct. 1, 2009; U.S. Patent Application Publication No. 2010/0256558 published Oct. 7, 2010; and U.S. Patent Application Publication No. 2011/0015569 published Jan. 20, 2011. Although particular embodiments of an RCGS 20 are described and illustrated in the aforementioned applications, it should be understood that RCGS 20 may assume a variety of different embodiments. For example, RCGS 20 may comprise any of the systems offered for sale by Hansen Medical, Inc. under the trademarks "Magellan" and "Sensei." RCGS 20 may also comprise a magnetic navigation system such as the system offered for sale by Stereotaxis, Inc. under the trademark "Epoch" in which magnetic fields are used to guide an ablation catheter having a magnetic member that is responsive to the generation of the magnetic fields.

Field generator 22 may be provided to allow for alternative external excitation of coils 44, 46, 48, 50. Although ECU 26 may be used to drive or excite coils 44, 46, 48, 50 through conductors 80 extending to coils 44, 46, 48, 50 it may alternatively be desired to excite coils 44, 46, 48, 50 using an external field generator (external to at least catheter 16, but potentially body 14 s well). Field generator 22 generates one or more magnetic fields. In one embodiment, field generator includes a set of three orthogonally arranged coils arranged to create magnetic fields within an area including body 14 and to control the strength, orientation and frequency of the fields. Field generator 22 may comprise a magnetic field generator such as the MediGuide™ Technology offered for sale by St. Jude Medical, Inc. or the generator sold under the trademark "CARTO" by Biosense Webster, Inc.

Display system 24 is provided to convey information to a physician to assist in diagnosis and treatment. Display system 24 may comprise one or more conventional computer monitors or other display devices. Display system 24 presents a graphical user interface (GUI) to the physician. The GUI may include a variety of information including, for example, an image of the geometry of tissue 12, electrophysiology data associated with the tissue 12, graphs illustrating voltage levels over time for various electrodes 42 and images of catheter 16 and other medical devices and related information indicative of the position of catheter 16 and other devices relative to the tissue 12.

ECU 26 provides a means for controlling delivery of ablation energy by ablation catheter 16 to tissue 12 and for controlling the operation of various components of system 10 including catheter 16, ablation generator 18, RCGS 20, field generator 22 and display system 24. ECU 26 may further form part of a system for determining the position and orientation of catheter 16 and similar devices within body 14 such as the system offered for sale under the trademark EnSite™ NavX™ by St. Jude Medical, Inc. and described in U.S. Pat. No. 7,263,397, the entire disclosure of which is incorporated herein by reference or the system such as the MediGuide™ Technology offered for sale by St. Jude Medical, Inc. and generally shown and described in, for example, U.S. Pat. No. 7,386,339, the entire disclosure of which is incorporated herein by reference. ECU 26 may comprise one or more programmable microprocessors or microcontrollers or may comprise one or more ASICs. ECU 26 may include a central processing unit (CPU) and an input/output (I/O) interface through which ECU 26 may receive a plurality of input signals including signals generated by ablation generator 18, electrodes 42 and coils 44, 46, 48, 50 on catheter 16, and RCGS 20 and generate a plurality of output signals including those used to control and/or provide data to electrodes 42 and coils 44, 46, 48, 50 on catheter 16, ablation generator 18, RCGS 20, field generator 22 and display system 24.

In accordance with one aspect of the present teachings, ECU 26 provides a means for determining a contact force between the distal end 40 of catheter 16 and tissue 12. ECU 26 may be configured with programming instructions from a computer program (i.e., software) to implement various methods for determining a contact force between the distal end 40 of catheter 16 and tissue 12. The program may be stored in a local memory associated with ECU 26, a remote memory accessible by ECU 26 over a telecommunications network (e.g., on a file server) or on a portable storage medium such as a compact disc or on other types of computer readable storage mediums. ECU 26 determines the contact force responsive to signals generated by coils 44, 46, 48, 50 on catheter 16 that are indicative of a change in an electrical characteristic of coils 44, 46, 48, 50. As discussed hereinabove, the position of coil 50 relative to coils 44, 46, 48 has an effect on an electrical characteristic (e.g., an inductance related characteristic) associated with each coil 44, 46, 48. In the absence of any contact force between the distal end 40 of catheter 16 and tissue 12 (i.e. in an uncompressed and unbent state), the electrical characteristic has one value. Movement of distal portion 70 of shaft 36 and, therefore, movement of coil 50 typically causes changes in each of the electrical characteristics of coils 44, 46, 48 such that the electrical characteristics assume new values. These changes in the electrical characteristics provide an indication of the contact force between the distal end 40 of catheter 16 and tissue 12 and the position and orientation of the distal end 40 of catheter 16. ECU 26 may be configured to measure changes in a variety of electrical characteristics associated with coils 44, 46, 48 including inductance, the resonant frequency of each coil 44, 46, 48 the inductive or capacitive coupling of each coil 44, 46, 48 or the loss in resistance in each coil 44, 46, 48. As an example, an equal change in an electrical characteristic on all three coils 44, 46, 48 indicates a uniform compression of the distal portion 70 of shaft 36 whereas any unequal changes corresponding to a bending of distal portion 70. Referring to FIGS. 5-8, a brief overview of some exemplary methods of determining contact force includes the following examples (several of which are described in greater detail hereinbelow): (1) referring to FIG. 5, ECU 26 may generate a current pulse in coil 50 producing response voltages across coils 44, 46, 48 or generate current pulses in coils 44, 46, 48 producing a response voltage across coil 50; (2) referring to FIG. 6, ECU 26 may generate a current pulse across coil pairs 44/50, 46/50 or 48/50 and measure the decay in each current as the combined magnetic fields collapse; (3) referring to FIG. 6, ECU 26 may generate a current pulse in coil 50 producing response voltages across coils 44, 46, 48 or generate current pulses in coils 44, 46, 48 producing a response voltage across coil 50; (4) referring to FIG. 7, ECU 26 may again generate a current pulse in coil 50 producing response voltages across coils 44, 46, 48 or generate current pulses in coils 44, 46, 48 producing a response voltage across coil 50; (5) referring to FIG. 8, ECU 26 may generate a current pulse in coil pair 44/50 and monitor the decay in current as the combined magnetic field collapses; (6) referring to FIG. 8, ECU 26 may generate a current in coil 50 producing a response voltage across coil 44 or generate a current pulse in coil 44 producing a response voltage across coil 50. A decay current, as mentioned above, can be monitored, for example, as a voltage across a resistor (not shown). An excited voltage in a coil resulting from current generated in another coil can be monitored using a voltage measurement circuit. The decay current or voltage can be measured at an instantaneous value at a certain time relative to the excitation of the coil or as an integrated value over time since the excitation. It should be understood that the use of two coils as in FIG. 8 will produce a combined magnetic field which is a function of the angulation and distance of the two coils relative to each other. Thus, even connected, codriven coils can be used as a force sensor. By using three sensing coils, a 3D force vector determination can be made (whereas the use of a single sensing coil as in FIG. 8 will give a single answer representing combined axial and bending force).

Figure 9:
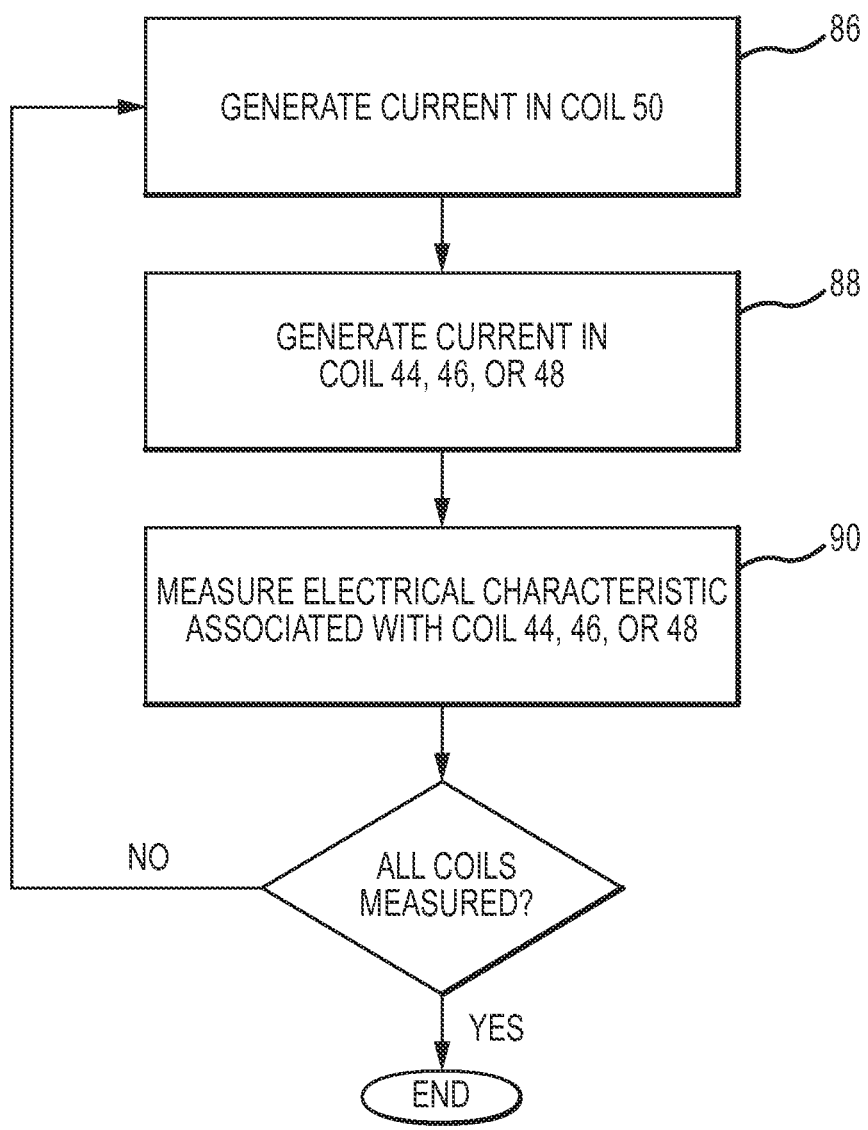
FIG. 9 is a flow chart diagram illustrating a system and method for diagnosis or treatment of tissue in a body in accordance with one embodiment of the present teachings.

Referring now to FIG. 9, one embodiment of a system and method in accordance with the present teachings is illustrated. In this embodiment, coils 44, 46, 48, 50 are wound as illustrated in FIG. 5 with each end of each coil 44, 46, 48, 50 having a separate conductor 80. ECU 26 may first implement a process 86 of generating a current in coil 50 to create an electromagnetic field. ECU 26 may then simultaneously implement a process 88 of generating a current in one of coils 44, 46, 48 to create another electromagnetic field opposing the electromagnetic field generated by the current in coil 50. The opposed electromagnetic fields may be created by winding coils in different directions or provide current in different directions. The field generated by the current in coil 44, 46, or 48 is intended to at least partially cancel the magnetic field generated by the current in coil 50. Even in the absence of a contact force on distal end 40 of catheter 16, generating a current in coil 50 and creation of the resulting magnetic field will induce a current in coils 44, 46, 48. Simultaneously, generating an opposing magnetic field by applying a current to one or more of coils 44, 46, 48 results in a smaller summed net electromagnetic field. Deflection of coil 50 will then reduce field cancellation and result in an increasingly large net electromagnetic field starting at a low value. A system in accordance with this embodiment of the present teachings is therefore more sensitive and advantageous relative to conventional systems because it nearly eliminates the summed net magnetic field of paired coils 44/50, 46/50 and 48/50 that exists in the absence of any contact force and deflection. The current sufficient to generate the cancelling field in coil 44, 46 and/or 48 can be determined by testing catheter 16 during manufacture or prior to a medical procedure. In order to generate the cancelling field, one or more of coils 44, 46, 48 may be wound in the opposite direction relative to coil 50 or the currents applied to coil 50 and coil 44, 46 and/or 48 may be run in opposite directions along coils 50 and 44, 46, 48. As distal portion 70 of catheter 16 deflects from axis 74, the opposing field will become less effective in negating the field generated by coil 50 so the detectable summed net field gets larger with deflection from a small starting value. When distal portion 70 is compressed due to a contact force, the summed fields of individual coil pairs 44/50, 46/50 and 48/50, presuming the same winding and current direction as above, negate even more thereby reducing their summed magnetic field. Once the currents are provided and the summed field established, ECU 26 may implement the process 90 of measuring an electrical characteristic associated with coil 44, 46 or 48 that is indicative of deformation of spring 76 or other flexible member and distal portion 70 and a specific contact force between distal portion 70 and tissue 12. This process may include halting the generation of current and monitoring current decay as the summed field collapses. Steps 86, 88, 90 may then be repeated for each of coils 44, 46, 48. Although the above described embodiment, generates a cancelling field by generating a current in one of coils 44, 46, 48, it should be understood that the canceling field could alternatively be generated by generating currents in multiple coils 44, 46, 48.

Figure 10:
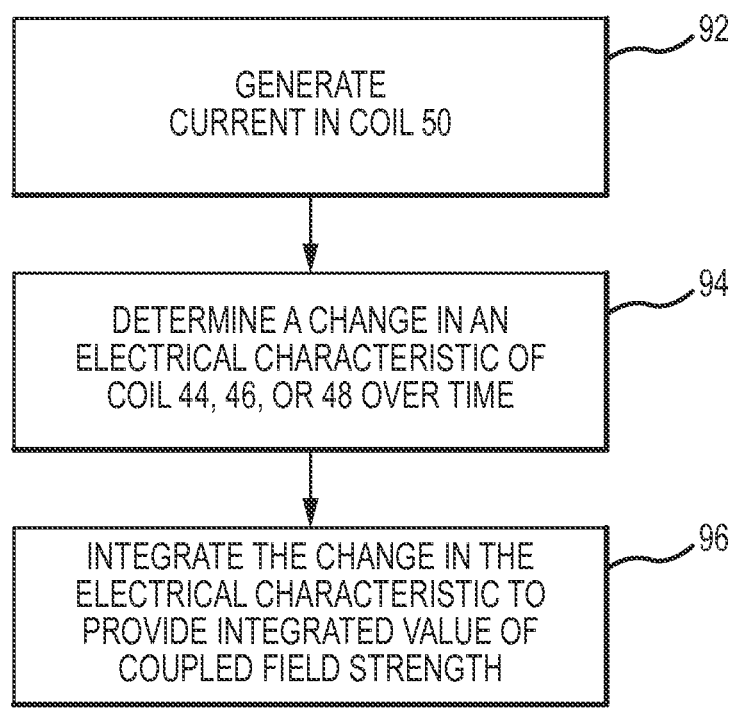
FIG. 10 is a flow chart diagram illustrating a system and method for diagnosis or treatment of tissue in a body in accordance with another embodiment of the present teachings.

Referring now to FIG. 10, another embodiment of a system and method in accordance with the present teachings is illustrated. In this embodiment, coils 44, 46, 48, 50 are again wound as illustrated in FIG. 5 with each end of each coil 44, 46, 48, 50 having a separate conductor 80. ECU 26 may first implement a process 92 of generating a current in coil 50. ECU 26 may then implement a process 94 of determining a change in an electrical characteristic associated with one or more of coils 44, 46, 48 over a period of time of decay in an electromagnetic field generated as a result of the current in coil 50. ECU 26 may then implement a process 96 of integrating the change in the electrical characteristic to obtain an integrated value of a coupled field strength of the electromagnetic field that is indicative of the amount of deformation of spring 76 or another flexible member and distal portion 70 of catheter 16 at the time current was supplied to coil 50.

Figure 11:
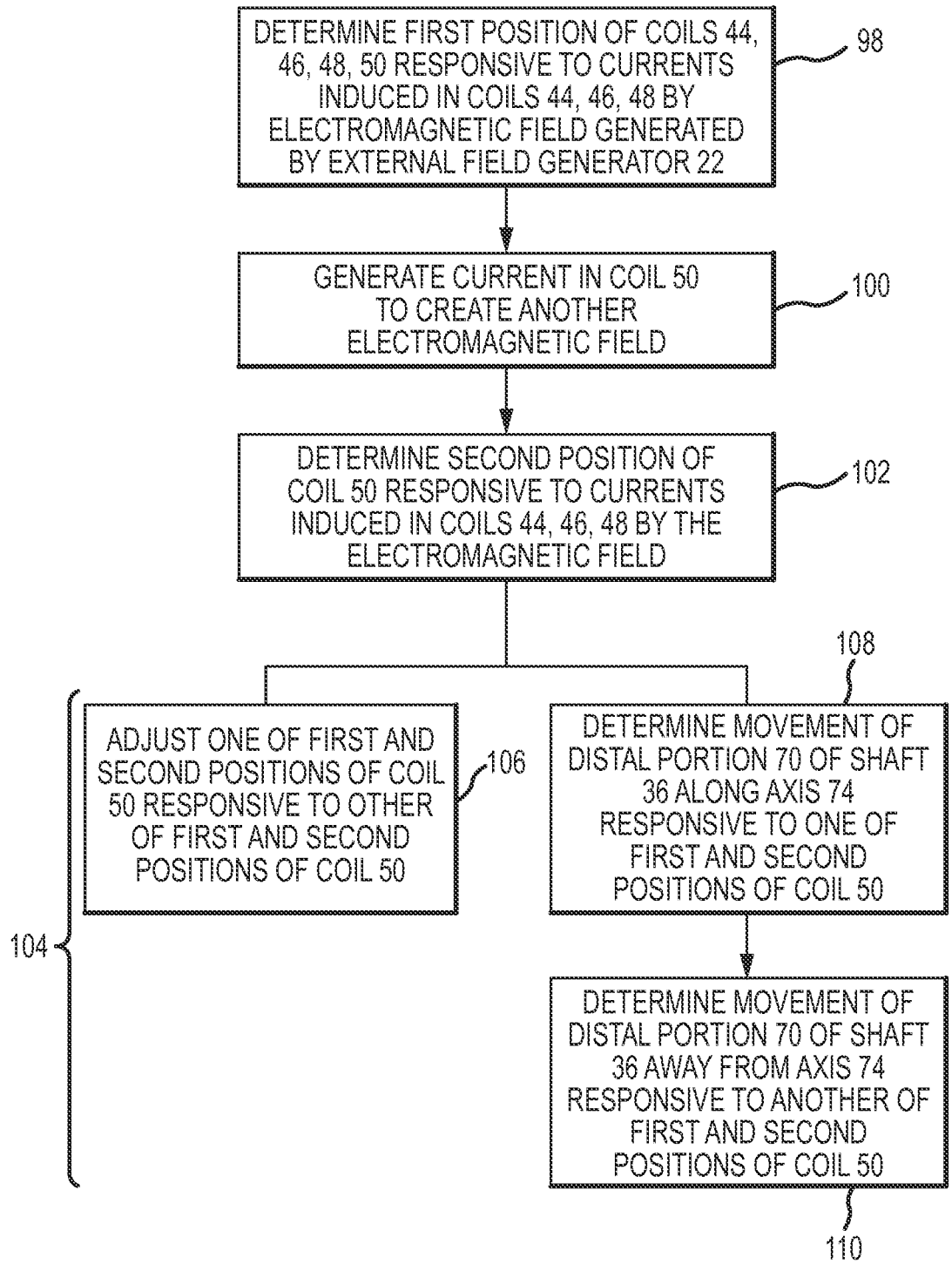
FIG. 11 is a flow chart diagram illustrating a system and method for diagnosis or treatment of tissue in a body in accordance with another embodiment of the present teachings.

Referring now to FIG. 11, another embodiment of a system and method in accordance with the present teachings is illustrated. In this embodiment, coils 44, 46, 48, 50 are again wound as illustrated in FIG. 5 with each end of each coil 44, 46, 48, 50 having a separate conductor 80. This embodiment makes use of position measurements obtained using magnetic fields generated both internally within catheter 16 and externally from catheter 16. In particular, this embodiment involves generating currents in coils 44, 46, 48, 50 using conductors 80 and determining contact force as taught hereinabove and/or hereinbelow. The embodiment further involves generating current in coils 44, 46, 48, 50 using field generator 22 and determining the position in space (to at least five degrees of freedom) as done for surgical navigation and using the positional data to determine the relative angles and displacements of coils 44, 46, 48, 50 to provide a second independent determined of contact force. ECU 26 may implement a process 98 of determining a first position for each of coils 44, 46, 48, 50 responsive to currents induced in coils 44, 46, 48, 50 by an electromagnetic field generated by external field generator 22. ECU 26 may, for example, determine the position s of each coil in response to the currents induced by the generated magnetic fields by implementing the MediGuide™ Technology offered for sale by St. Jude Medical, Inc. and generally shown and described in, for example, U.S. Pat. No. 7,386,339, the entire disclosure of which is incorporated herein by reference. Process 98 may include the subprocess of averaging position data for coils 44, 46, 48 to improve the accuracy of the position measurements. In particular, when coils 44, 46, 48 are parallel, the deflection relative to axis 74 should be the same for all three coils 44, 46, 48. Therefore, the dimensions relating to deflection can be averaged and the average value assigned to each coil 44, 46, 48 as part of the first position. ECU 26 may further implement the processes 100, 102 of generating a current in coil 50 to create another electromagnetic field and determining a second position for coil 50 responsive to the currents induced in coils 44, 46, 48 by the electromagnetic field. As discussed in greater detail hereinabove, the currents induced in coils 44, 46, 48 are indicative of the deformation of spring 76 or another flexible member and the deformation of distal portion 70 of shaft 36. ECU 26 may further implement the process 104 of determining a contact force between the distal portion 70 of shaft 36 and tissue 12 responsive to the determined positions of coils 44, 46, 48, 50. Process 104 may be implemented in a variety of ways. In accordance with one embodiment, process 104 may implement the subprocess 106 of adjusting the first position of coil 50 (determined with reference to fields created by external generator 22) responsive to the second position of coil 50 (determined with reference to fields created within catheter 16) or, alternatively, adjusting the second position of coil 50 responsive to the first position of coil 50. Process 104 may, for example, including averaging of the first and second positions of the coil 50 over time to reduce noise. In accordance with another embodiment, process 104 may implement the subprocess 108 of determining a movement of distal portion 70 of shaft 36 along axis 74 responsive to one of the first and second positions of coil 50 and the subprocess 110 of determining a movement of distal portion 70 of shaft 36 towards or away from axis 74 responsive to the other of the first and second positions of coil 50. For example, in one embodiment movement of distal portion 70 along axis 74 may be determined responsive to the second position of coil 50 determined using internally generated magnetic fields while movement of distal portion 70 away from axis 74 may be determined responsive to the first position of coil 50 determined using externally generated magnetic fields. Alternatively, movement along axis 74 may be determined responsive to the first position of coil 50 while movement away from axis 74 may be determined responsive to the second position of coil 50. Finally, it should be noted that having two independent sources of coil response information allows one to deconvolute axial and bending deflections when using only a two-coil winding arrangement as in FIG. 8. Although each of coils 44, 46, 48, 50 is wound in the same direction in FIG. 5, it should be understood that one or more of coils 44, 46, 48, 50 could be wound in opposing directions as discussed hereinabove to permit generation of fields that at least partially cancel one another in accordance with various embodiments disclosed in FIG. 9. A system and method in accordance with this embodiment of the present teachings is advantageous as compared to conventional systems because the system improves the accuracy of contact force measurements by using position information from multiple field generators both within and outside of catheter 16.

Figure 12:
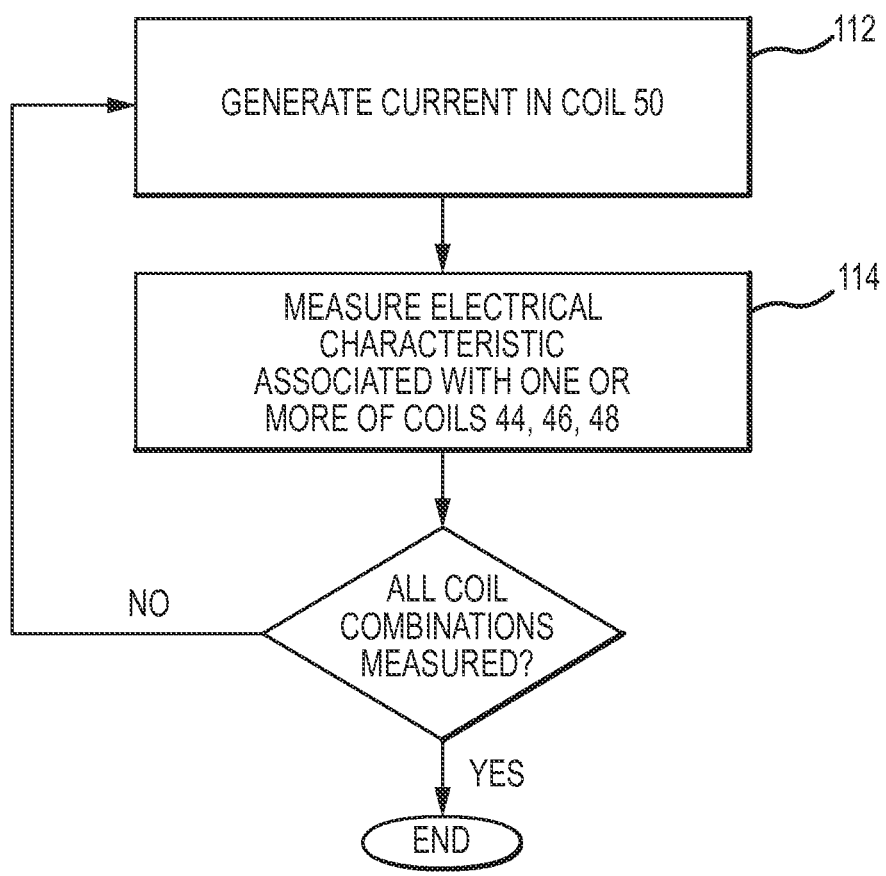
FIG. 12 is a flow chart diagram illustrating a system and method for diagnosis or treatment of tissue in a body in accordance with another embodiment of the present teachings.

Referring now to FIG. 12, another embodiment of a system and method in accordance with the present teachings is illustrated. In this embodiment, coils 44, 46, 48, 50 are wound as illustrated in FIG. 6 with coil 50 being wound in series with each of coils 44, 46, 48 such that one end of coil 50 and one end of each of coils 44, 46, 48 are coupled together at a common node 84 or wound as illustrated in FIG. 7 with one end of each of coils 44, 46, 48 coupled together at a common node 85. In each case, an additional conductor 80 is also coupled to node 84 or node 85. ECU 26 may implement a process 112 of generating a current in coil 50. In the embodiment shown in FIG. 6, current is generated in coil 50 using conductors 80 attached to coil 50 and node 84. In the embodiment shown in FIG. 7, current is generated in coil 50 using conductors 80 attached to either end of coil 50. Alternatively, current may be induced in coils 50 using field generator 22. ECU may then implement a process 114 of measuring an electrical characteristic associated with one or more of coils 44, 46, 48 such as the voltages across coils 44, 46, 48. In the embodiment shown in FIG. 6, ECU 26 measures the voltage across terminals at the end of conductors 80 attached to one end of a corresponding coil 44, 46, 48 and to node 84. In the embodiment shown in FIG. 7, ECU 26 measures the voltage across terminals at the end of conductors 80 attached to one end of a corresponding coil 44, 46, 48 and to node 85. The electrical characteristic will be indicative of deformation of the spring 76 or other flexible member and the specific contact force between the distal portion of shaft 36 and tissue 12. It should be understood that ECU 26 may alternatively generate a current in any of coils 44, 46, 48 and measure an electrical characteristic associated with coil 50 such as the voltage across coil 50. Further, it should be understood that the same process may be implemented with fewer or greater than three coils 44, 46, 48 including the coil winding arrangement shown in FIG. 8.

Figure 13:
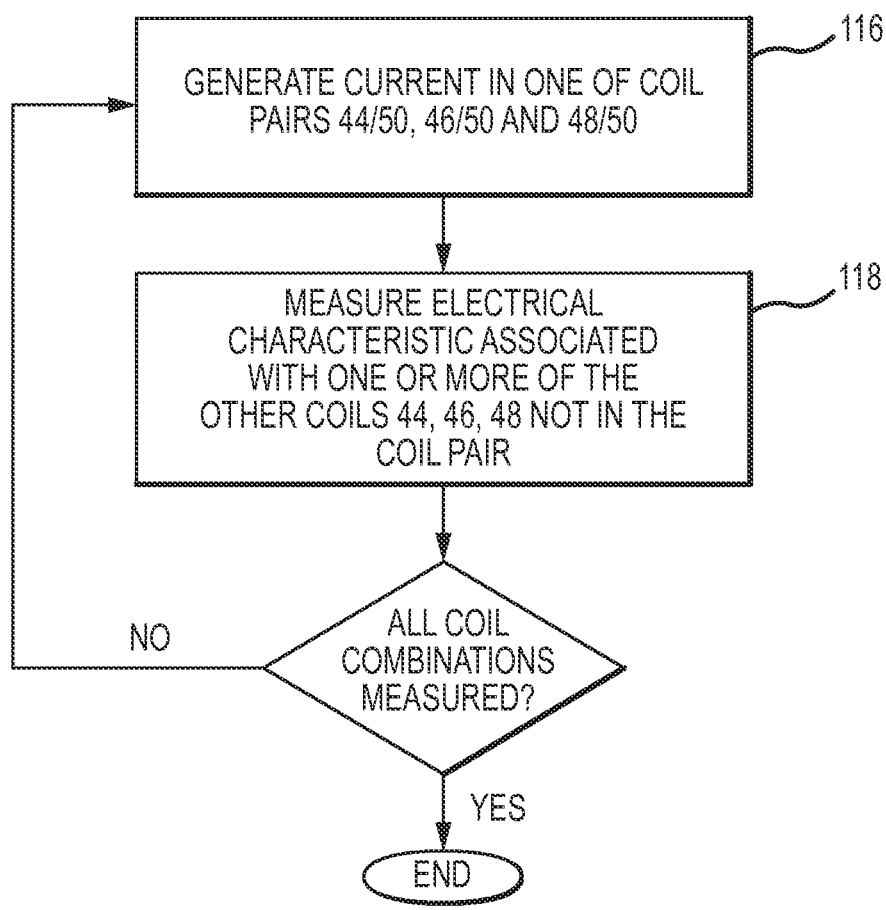
FIG. 13 is a flow chart diagram illustrating a system and method for diagnosis or treatment of tissue in a body in accordance with another embodiment of the present teachings.

Referring now to FIG. 13, another embodiment of a system and method in accordance with the present teachings is illustrated. In this embodiment, coils 44, 46, 48, 50 are again wound as illustrated in FIG. 6. ECU 26 may implement a process 116 of generating a current in a pair of coils such as coils 44, 50. The current may be generated in such a way that the magnetic fields generated by current in coils 44, 50 are additive or subtractive (i.e. at least partially cancel one another) by, for example, winding coils 44 and 50 in opposite directions. The current may be generated by directing current along conductors 80 to coils 44, 50 or by inducing current in coils 44, 50 using field generator 22. ECU 26 may then implement a process 118 of measuring an electrical characteristic associated with one or more of coils 46, 48 such as the voltages across coils 46, 48 as described hereinabove. The electrical characteristic associated with coils 46, 48 is indicative of deformation of the spring 76 or other flexible member and the specific contact force between the distal portion of shaft 36 and tissue 12. ECU 26 may repeat processes 116, 118 for each combination of coils. For examples, ECU 26 may first generate current in coils 44, 50 and measure electrical characteristics associated with coils 46, 48, then generate current in coils 46, 50 and measure electrical characteristics associated with coils 44, 48 and finally generate current in coils 48, 50 and measure electrical characteristics associated with coils 44, 46. It should be understood that ECU 26 may alternatively generate a current in any of coils 44, 46, 48 and measure an electrical characteristic associated with the combination of coil 50 and another of coils 44, 46, 48 such as the voltage across the combination of coils. A system in accordance with this embodiment of the present teachings is advantageous relative to conventional systems because it provides a means for measuring contact force between catheter 16 and tissue 12 in body 14 that is less complex and less expensive than conventional systems. In particular, the use of series connected coils 44, 46, 48, 50 enables a contact force to be determined while reducing the number of conductors 80 needed within catheter 16 as compared to conventional systems. As a result, the system conserves valuable space within catheter 16 and is less expensive to manufacture.

Figure 14:
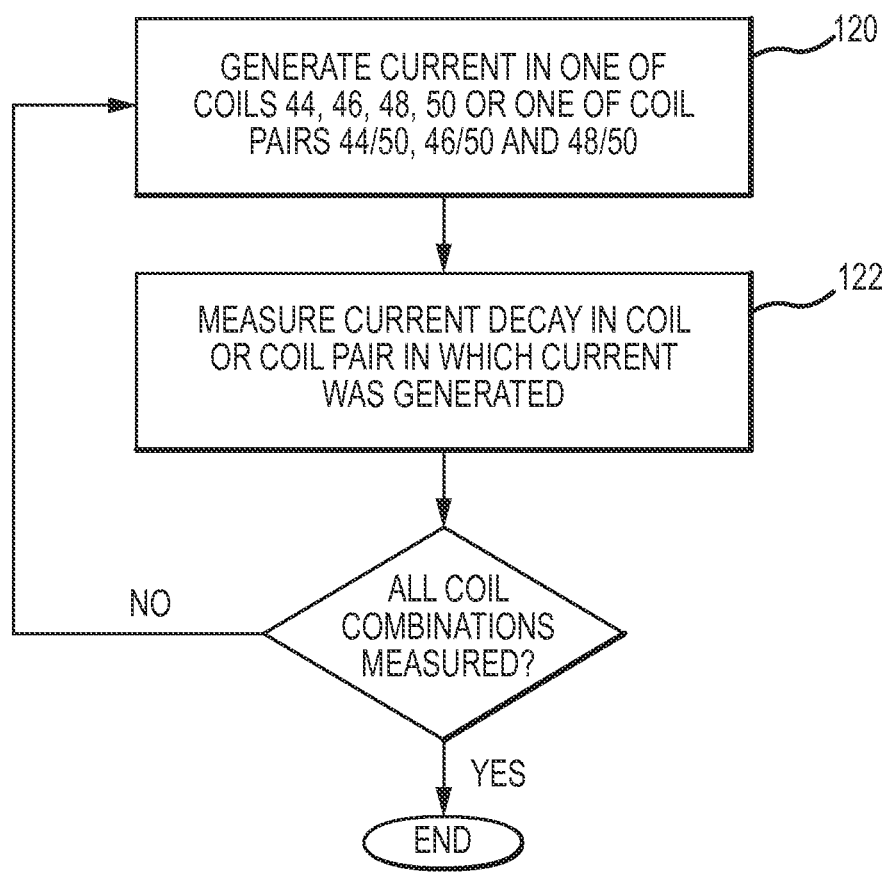
FIG. 14 is a flow chart diagram illustrating a system and method for diagnosis or treatment of tissue in a body in accordance with another embodiment of the present teachings.

Referring now to FIG. 14, another embodiment of a system and method in accordance with the present teachings is illustrated. In this embodiment, coils 44, 46, 48, 50 are wound as illustrated in FIG. 6 with coil 50 being wound in series with each of coils 44, 46, 48 such that one end of coil 50 and one end of each of coils 44, 46, 48 are coupled together at a common node 84 or wound as illustrated in FIG. 7 with one end of each of coils 44, 46, 48 coupled together at a common node 85. ECU 26 may implement a process 120 of generating a current in any of coils 44, 46, 48, 50 or, in the embodiment of FIG. 6, a pair of coils such as coils 44, 50. In the latter case, the current may be generated in such a way that the magnetic fields generated by current in coils 44, 50 are additive or subtractive (i.e. at least partially cancel one another) by, for example, winding coils 44 and 50 in opposite directions. The current may be generated by directing current along conductors 80 to coils 44, 46, 48, 50 or by inducing current in coils 44, 46, 48, 50 using field generator 22. ECU 26 may then implement a process 122 of measuring a decay in the current in the excited coil 44, 46, 48, 50 or combination of coils (e.g., coils 44, 50). The current decay may be measured by measuring the voltage across resistors in series with each of coils 44, 46, 48, 50. The decay of current in coils 44, 46, 48, and/or 50 is indicative of deformation of the spring 76 or other flexible member and the specific contact force between the distal portion of shaft 36 and tissue 12. ECU 26 may repeat processes 120, 122 for each coil 44, 46, 48, 50 or combination of coils 44, 46, 48, 50. A system in accordance with this embodiment of the present teachings is again advantageous relative to conventional systems because it provides a means for measuring contact force between catheter 16 and tissue 12 in body 14 that is less complex and less expensive than conventional systems. In particular, the use of series connected coils 44, 46, 48, 50 in FIGS. 6 and 8 and/or coils connected at one end in FIG. 7 enables a contact force to be determined while reducing the number of conductors 80 needed within catheter 16 as compared to conventional systems. As a result, the system conserves valuable space within catheter 16 and is less expensive to manufacture.

Figure 15:
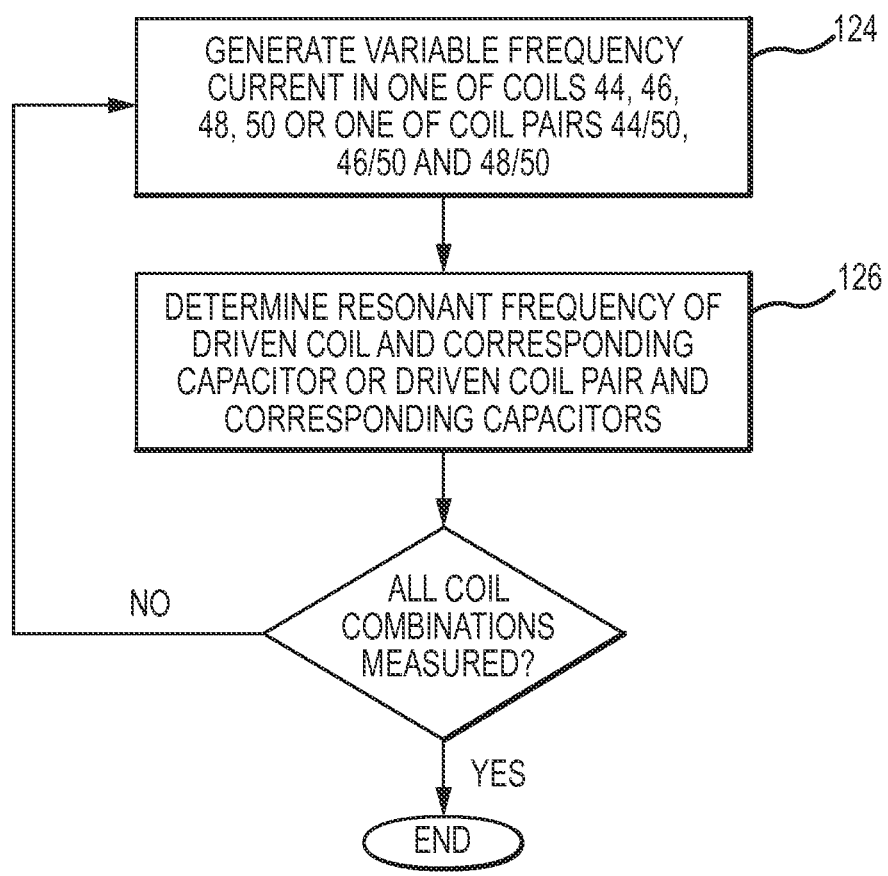
FIG. 15 is a flow chart diagram illustrating a system and method for diagnosis or treatment of tissue in a body in accordance with another embodiment of the present teachings.

Referring now to FIG. 15, another embodiment of a system and method in accordance with the present teachings is illustrated. In this embodiment, coils 44, 46, 48, 50 are wound as illustrated in FIG. 6 with coil 50 being wound in series with each of coils 44, 46, 48 such that one end of coil 50 and one end of each of coils 44, 46, 48 are coupled together at a common node 84 or wound as illustrated in FIG. 7 with one end of each of coils 44, 46, 48 coupled together at a common node 85. Further, each coil 44, 46, 48, 50 includes a capacitor (not shown) in series with the coil 44, 46, 48, 50. ECU 26 may implement a process 124 of generating a variable frequency current in any of coils 44, 46, 48, 50 or, in the embodiment of FIG. 6, a pair of coils such as coils 44, 50. The current may be generated by directing current along conductors 80 to coils 44, 46, 48, 50 or by inducing current in coils 44, 46, 48, 50 using field generator 22. ECU 26 may then implement a process 126 of determining a resonant frequency for the coil 44, 46, 48, 50 and corresponding capacitor. The resonant frequency of each coil 44, 46, 48, 50 and corresponding capacitor varies with changing inductance resulting from deformation of the distal portion of shaft 36. Therefore, changes in the resonant frequency are indicative of deformation of the spring 76 or other flexible member and the specific contact force between the distal portion of shaft 36 and tissue 12. The nominal resonant frequency for each coil 44, 46, 48, 50 and corresponding capacitor in the absence of any contact force may be the same. Alternatively, however, the nominal resonant frequency for each coil 44, 46, 48, 50 and corresponding capacitor in the absence of any contact force may be made different (e.g., by placing different capacitors in series with each coil 44, 46, 48, 50). Employing different nominal resonant frequencies allows the use of even fewer conductors 80 in catheter 16. With reference to FIG. 7, for example, capacitors could be coupled to the end of each coil 44, 46, 48 opposite the ends of coils 44, 46, 48 coupled to node 85 and a single conductor 80 could be coupled to the capacitors at a common node because only a single coil 44, 46, 48 and corresponding capacitor would be resonant at a given time despite the common connections. ECU 26 may repeat processes 124, 126 for each coil 44, 46, 48, 50 or combination of coils 44, 46, 48, 50. A system in accordance with this embodiment of the present teachings is again advantageous relative to conventional systems because it provides a means for measuring contact force between catheter 16 and tissue 12 in body 14 that is less complex and less expensive than conventional systems. In particular, the use of series connected coils 44, 46, 48, 50 in FIGS. 6 and 8 and/or coils connected at one end in FIG. 7 enables a contact force to be determined while reducing the number of conductors 80 needed within catheter 16 as compared to conventional systems. As a result, the system conserves valuable space within catheter 16 and is less expensive to manufacture.

Although several embodiments of this disclosure have been described above with a certain degree of particularity, those skilled in the art could make numerous alterations to the disclosed embodiments without departing from the scope of this disclosure. All directional references (e.g., upper, lower, upward, downward, left, right, leftward, rightward, top, bottom, above, below, vertical, horizontal, clockwise and counterclockwise) are only used for identification purposes to aid the reader's understanding of the present disclosure, and do not create limitations, particularly as to the position, orientation, or use of the disclosed embodiments. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the spirit of the disclosure.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:
1. A system for the treatment or diagnosis of tissue within a body, comprising:
   a medical device, comprising:
      an elongate, tubular shaft configured to be received within the body, said shaft having a proximal portion and a distal portion configured for movement relative to the proximal portion including by movement towards and away from the proximal portion along a longitudinal axis of said shaft and by deflection from the longitudinal axis;

a flexible member disposed between the proximal and distal portions of said shaft, said flexible member having a predetermined stiffness;

a first electromagnetic coil disposed within said shaft;

a second electromagnetic coil disposed within said shaft and configured for movement with the distal portion of said shaft and relative to the first electromagnetic coil;

third and fourth electromagnetic coils disposed within said shaft, each of said third and fourth electromagnetic coils connected to the second electromagnetic coil via a common node; and, an electronic control unit configured to determine a specific contact force between the distal portion of said shaft and the tissue, responsive to signals generated by at least one of said first, second, third, and fourth electromagnetic coils.

2. The system of claim 1 wherein said electronic control unit is further configured, in determining the specific contact force, to:

generate a current in said first electromagnetic coil; and measure an electrical characteristic associated with at least one of said second, third, and fourth electromagnetic coils, said electrical characteristic indicative of deformation of said flexible member and the specific contact force between the distal portion of said shaft and the tissue.

3. The system of claim 1 wherein said electronic control unit is further configured, in determining the specific contact force, to:

generate a current in at least one of said first, second, third, and fourth electromagnetic coils; and measure a decay of said current in at least one of said first, second, third, and fourth electromagnetic coils, said decay indicative of deformation of said flexible member and the specific contact force between the distal portion of said shaft and the tissue.

4. The system of claim 1, wherein said electronic control unit is further configured, in determining the specific contact force, to:

generate a current in at least one of said second, third, and fourth electromagnetic coils; and measure an electrical characteristic associated with said first electromagnetic coil, said electrical characteristic indicative of deformation of said flexible member and the specific contact force between the distal portion of said shaft and the tissue.

5. The system of claim 1, wherein said electronic control unit is further configured, in determining the specific contact force, to:

generate a current in said first and second electromagnetic coils; and, measure an electrical characteristic associated with each of said third and fourth electromagnetic coils, said electrical characteristic indicative of deformation of said flexible member and the specific contact force between the distal portion of said shaft and the tissue.

6. The system of claim 1, wherein said electronic control unit is further configured, in determining the specific contact force, to:

generate a current in said third electromagnetic coil; and, measure an electrical characteristic associated with a combination of said first and second electromagnetic coils, said electrical characteristic indicative of deformation of said flexible member and the specific contact force between the distal portion of said shaft and the tissue.

7. The system of claim 1, further comprising a capacitor coupled to at least one of said first, second, third, and fourth electromagnetic coils and wherein said electronic control unit is further configured, in determining the specific contact force, to:

determine a resonant frequency of said at least one of said first, second, third, and fourth electromagnetic coils and said corresponding capacitor, said resonant frequency indicative of deformation of said flexible member and the specific contact force between the distal portion of said shaft and the tissue.

8. The system of claim 1, wherein each of the second, third, and fourth electromagnetic coils are coupled at only one end to a conductor.

9. The system of claim 1, further comprising:

a first conductor coupled to a first end of the first electromagnetic coil;

a second conductor coupled to a second end of the first electromagnetic coil;

a third conductor coupled to an end of the second electromagnetic coil;

a fourth conductor coupled to an end of the third electromagnetic coil;

a fifth conductor coupled to an end of the fourth electromagnetic coil; and a sixth conductor coupled to the common node.

* * * * *